(12) United States Patent
Biel et al.

(10) Patent No.: US 10,624,981 B2
(45) Date of Patent: Apr. 21, 2020

(54) METHOD AND SYSTEM FOR REMOVING A LIQUID FROM A CONTAINER FOR ACCOMMODATING AN OPHTHALMIC LENS

(71) Applicant: Novartis AG, Basel (CH)

(72) Inventors: Roger Biel, Aschaffenburg (DE); Andrea Kopp, Aschaffenburg (DE); Katrin Sylke Struckmeier, Aschaffenburg (DE); Michael Stutz, Kleinwallstadt (DE)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 16/226,990

(22) Filed: Dec. 20, 2018

(65) Prior Publication Data

US 2019/0117821 A1  Apr. 25, 2019

Related U.S. Application Data

(62) Division of application No. 15/350,374, filed on Nov. 14, 2016, now Pat. No. 10,195,303.

(60) Provisional application No. 62/266,034, filed on Dec. 11, 2015.

(51) Int. Cl.
| | |
|---|---|
| *A61L 12/08* | (2006.01) |
| *B29D 11/00* | (2006.01) |
| *F26B 5/12* | (2006.01) |
| *B08B 3/08* | (2006.01) |

(52) U.S. Cl.
CPC .............. *A61L 12/086* (2013.01); *B08B 3/08* (2013.01); *B29D 11/00125* (2013.01); *B29D 11/00259* (2013.01); *F26B 5/12* (2013.01); *B29D 11/0023* (2013.01); *B29D 11/0025* (2013.01)

(58) Field of Classification Search
CPC ...................................... A61L 12/086
See application file for complete search history.

(56) References Cited

U.S. PATENT DOCUMENTS

2017/0165393 A1\* 6/2017 Biel ...................... A61L 12/086

\* cited by examiner

*Primary Examiner* — Jason Y Ko
(74) *Attorney, Agent, or Firm* — Patrick M. Ryan

(57) ABSTRACT

A method of removing a liquid from a container (1) for accommodating an ophthalmic contact lens, in particular a soft contact lens, during transporting the container (1) from a liquid bath (13) to a subsequent processing station (14), the method including the steps of:
  transporting the container (1) from the liquid bath to the subsequent processing station,
  generating suction (20), and
  applying the suction (20) to a bottom (11) of the container (1) during the step of transporting the container (1) from the liquid bath to the subsequent processing station, thereby removing the liquid from the container (1).

3 Claims, 3 Drawing Sheets

METHOD AND SYSTEM FOR REMOVING A LIQUID FROM A CONTAINER FOR ACCOMMODATING AN OPHTHALMIC LENS

This application is a Divisional of U.S. patent application Ser. No. 15/350,374, filed Nov. 14, 2016, which claims the benefit under 35 USC 119(e) of U.S. provisional application Ser. No. 62/266,034 filed on Dec. 11, 2015, the contents of each of which are incorporated herein by reference in their entireties.

FIELD OF THE INVENTION

The present invention relates to a method and a system for removing a liquid from a container for accommodating an ophthalmic lens, in particular a contact lens such as a soft contact lens.

BACKGROUND OF THE INVENTION

Contact lenses, particularly soft contact lenses, are generally manufactured in automated production processes well-known in the art. Depending on the lens forming materials used and also depending on the method of manufacturing, the contact lenses have to be immersed in various liquids such as extraction liquids, rinsing liquids, coating liquids, etc., to obtain the final contact lens which is suitable to be worn in direct contact with the wearer's eye. For that purpose, it is known to transport the contact lenses through several baths containing such liquids. For example, the contact lenses are introduced into containers arranged in a transport carrier which is moved along the length of the individual baths such that the contact lenses contained in the respective containers are exposed to the liquids of the respective baths. For example, after having been transported through one liquid bath the containers arranged in the transport carrier are transferred to a further liquid bath containing a further liquid. By way of example, the liquid baths may serve for lens rinsing, extraction, or coating purposes and may contain either the same kind of liquid, if necessary in different concentrations, or may contain liquids of different kind which are used for different purposes (see above).

US 2011/091642 A1 describes a method and apparatus for transporting contact lenses accommodated in respective containers through successively arranged treatment baths comprising an automatically operating transfer means for transferring the carriers from one dipping bath to the next dipping bath along the travel path.

US 2011/0089053 A1 discloses a container for the accommodation of a contact lens during lens treatment processes such as extraction and/or rinsing and/or coating processes. The container may either be molded in one piece or may comprise several individual pieces which are assembled to form a container. The container generally comprises an elongated tubular body and, at a distal and of the container, a bottom which protrudes convexly towards the outside of the container. The bottom is provided with a number of apertures which enable a flow of liquid into and out of the tubular body.

Once the container has reached the end of the respective bath, the container is lifted out of the liquid of the liquid bath for being transferred into the liquid of the subsequent liquid bath, or for being transferred to another subsequent processing station. During this transfer, liquid of the preceding liquid bath may remain adhered to the surface of the bottom of the container and on the contact lens itself accommodated in the container, and such liquid may either be carried over to the subsequent liquid bath or may be spilled in the production area. In case the container is transferred to a subsequent liquid bath, the corresponding liquid in the said subsequent liquid bath either may be of the same kind but may have a concentration that differs from the concentration of the liquid contained in the preceding bath, or the subsequent bath may contain a liquid of a different kind. Accordingly, the carry-over of liquid from the preceding bath may either change the concentration of the liquid in the subsequent liquid bath or may contaminate the liquid in the subsequent liquid bath. In the first case (subsequent liquid bath contains the same kind of liquid at different concentration), the concentration of the liquid of the subsequent liquid bath must be monitored and may have to be maintained through the addition of fresh liquid or through the addition of one or more of the constituents of the liquid. In the other case (subsequent liquid bath contains different kind of liquid), the liquid of the subsequent liquid bath may have to undergo complex purification or may have to be replaced in case the concentration of the "contaminant" in the subsequent liquid bath exceeds a predefined threshold concentration.

For example, prior to immersing the contact lenses in an extraction liquid, they are rinsed in a water bath. The rinsing of the contact lenses in water prevents or reduces the soiling of the extraction liquid. However, as the containers containing the contact lenses are transferred from the water bath to the extraction liquid bath, small amounts of water are carried over from the water bath to the extraction liquid bath. As a consequence, during the production of contact lenses the concentration of the extraction liquid bath is constantly reduced, so that after a certain time the extraction liquid bath must be purified or the "contaminated" extraction liquid must be replaced with fresh extraction liquid.

It is therefore an object of the invention to further improve the efficiency of the treatment of ophthalmic lenses such as contact lenses, in particular soft contact lenses, in liquid baths.

SUMMARY OF THE INVENTION

To achieve these objects, the present invention suggests a method and a system as specified by the features of the respective independent claims. Advantageous aspects of the method and system according to the invention are the subject of the dependent claims.

As regards the method, a method of removing a liquid from a container for accommodating an ophthalmic contact lens, in particular a contact lens such as a soft contact lens, during transporting the container from a liquid bath to a subsequent processing station is suggested. The method comprises the steps of:

transporting the container from the liquid bath to the subsequent processing station, generating suction, and applying the suction to a bottom of the container during the step of transporting the container from the liquid bath to the subsequent processing station, thereby removing the liquid from the container.

According to one aspect of the method according to the invention, the step of applying suction comprises providing an aspirator comprising a suction cup having a concave wall with at least one suction orifice arranged in the concave wall, applying the suction through the at least one suction orifice arranged in the concave wall of the suction cup, and moving the suction cup towards the bottom of the container with the concave wall of the suction cup facing the bottom of the container.

According to a further aspect of the method according to the invention, the bottom of the container has a convex shape, and the concave wall of the suction cup has a shape which corresponds to the convex shape of the bottom of the container.

According to still a further aspect of the method according to the invention, applying the suction to the bottom of the container allows a leakage stream to flow between the bottom of the container and the concave wall of the suction cup towards the at least one suction orifice in the concave wall of the suction cup.

According to yet a further aspect of the method according to the invention, the suction cup is moved towards the bottom of the container only to an extent that the suction cup does not contact the bottom of the container.

Still in accordance with a further aspect of the method according to the invention, the suction is applied to the bottom of the container during a time period in the range of 0.5 seconds to 2 seconds.

In particular, the air flow of the suction is in the range of from $2 \text{ m}^3$ to $8 \text{ m}^3$.

In a further aspect of the invention, the suction (underpressure) is in the range of up to 900 hPa (corresponding to 900 millibars), in particular in the range of 350 hPa to 750 hPa (corresponding to 350 millibars to 750 millibars).

In accordance with another aspect of the method according to the invention, the transport of the container from the liquid bath to the subsequent processing station is accomplished intermittently, and the suction is applied to the bottom of the container at the time the transport of the container is intermitted.

The term "intermittently" is to be understood in a sense that the transport of the containers is performed such that there are time periods in which the container is transported (moved) along the travel path and time periods where this transport of the container along the travel path is intermitted (interrupted).

As regards the system for removing a liquid from a container for accommodating an ophthalmic contact lens, in particular a soft contact lens, the system according to the invention comprises:

a transport carrier comprising a container having a bottom, a conveyor for transporting the transport carrier from a liquid bath to a subsequent processing station, an aspirator comprising a suction cup connected to a vacuum supply line, for applying suction to the bottom of the container, and a positioner for arranging the container relative to the suction cup such that the bottom of the container is exposed to the suction applied by the suction cup during operation, in order to remove the liquid from the container.

According to one aspect of the system according to the invention, the bottom of the container has a convex shape, and the suction cup of the aspirator has a concave wall with at least one suction orifice arranged in the concave wall. The convex shape of the bottom of the container and the shape of the concave wall of the suction cup correspond to allow for accommodating the convexly shaped bottom of the container in a cavity bounded by the concave wall of the suction cup.

According to a further aspect of the system according to the invention, the positioner comprises an actuator for linearly moving the suction cup of the aspirator towards and away from the bottom of the container.

According to one aspect of the system according to the invention, the actuator is a pneumatic linear drive.

The method according to the invention allows for more efficient treatment of the ophthalmic lens in the liquid of the respective liquid bath, as either no or only very little carry-over of treatment liquid from the preceding treatment bath may occur. This is due to the removal of a liquid by applying the suction to the bottom of the container during the step of transporting the container from the first treatment bath to the second treatment bath. As a result, contamination or dilution is prevented or at least very greatly reduced so that a replacement of purification of the treatment liquid in the treatment baths can be either prevented or very greatly reduced.

Using a suction cup which is connected to a vacuum supply line for removing the remaining treatment liquid from a preceding treatment bath by moving the suction cup towards the bottom of the container allows for very efficiently removing the liquid. In particular when the suction cup has a shape which corresponds to the shape of the bottom of the container for accommodating the bottom of the container, removing the remaining liquid is highly efficient.

Applying suction and at the same time allowing a leakage stream to flow between the convex bottom of the container and the concave wall of the suction cup towards the suction orifice in the concave wall of the suction cup assists in transporting away through the vacuum supply line any liquid which may adhere to the bottom of the container or on the surface of the lens. The liquid is drawn in through the at least one suction orifice arranged in the concave wall of the suction cup without damaging the contact lens accommodated in the container.

Keeping a small distance between the suction cup and the (typically convex) bottom of the container allows for the leakage stream to flow between the bottom of the container and the concave wall of the suction cup, thereby effectively removing any liquid adhering to the container.

The advantages of the system according to the invention and of the various aspects thereof correspond to those already discussed above in connection with the various aspects of the method according to the invention. Therefore, they are not reiterated here.

As used in the specification including the appended claims, the singular forms "a", "an", and "the" include the plural, unless the context explicitly dictates otherwise. When using the term "about" with reference to a particular numerical value or a range of values, this is to be understood in the sense that the particular numerical value referred to in connection with the "about" is included and explicitly disclosed, unless the context clearly dictates otherwise. For example, if a range of "about" numerical value a to "about" numerical value b is disclosed, this is to be understood to include and explicitly disclose a range of numerical value a to numerical value b. Also, whenever features are combined with the term "or", the term "or" is to be understood to also include "and" unless it is evident from the specification that the term "or" must be understood as being exclusive.

BRIEF DESCRIPTION OF THE DRAWINGS

Further advantageous aspects of the invention become apparent from the following description of embodiments of the invention with the aid of the drawings, in which.

DETAILED DESCRIPTION OF EMBODIMENTS

As used in this specification, the term "liquid" or "treatment liquid" comprises any type of liquid to which the ophthalmic lens, in particular a contact lens such as a soft contact lens, may be exposed during a contact lens manufacturing process, and include in particular liquids influencing the physical or chemical properties of the lens. Without being exhaustive, such treatment liquids may comprise extraction liquids, rinsing liquids, coating liquids or any other type of liquid and in particular also may comprise water.

Figure 1:
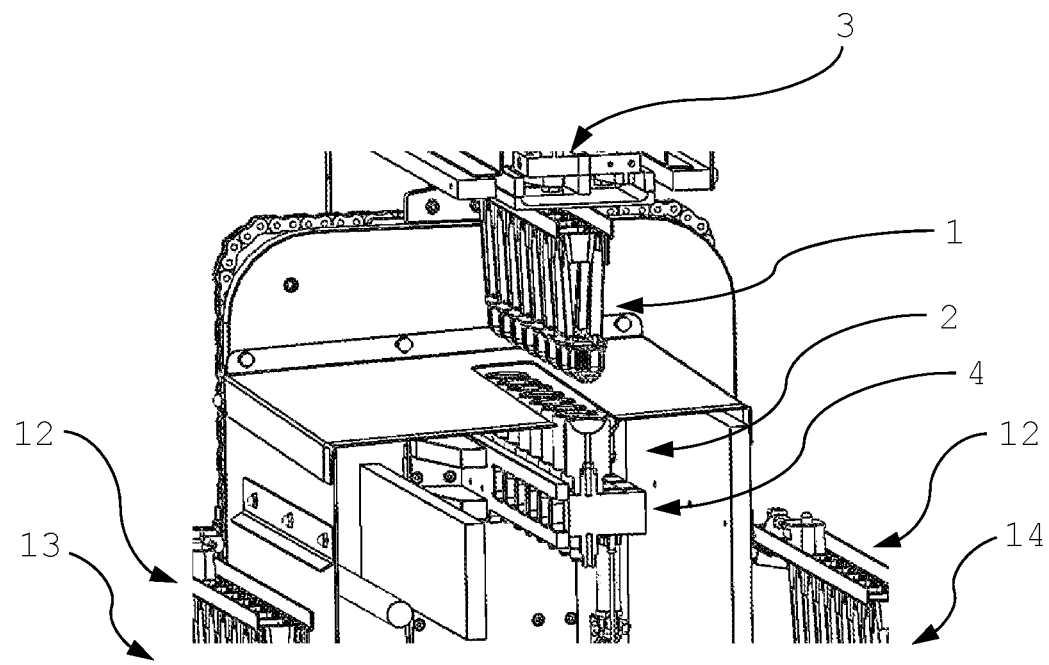
FIG. 1 is a cross-sectional perspective view of some essential components of an embodiment of the system according to the invention.

FIG. 1 shows in cross-sectional perspective view some essential components of a system according to one embodiment of the invention. As can be seen from FIG. 1, the system comprises a plurality of containers 1 each for accommodating a contact lens (not shown). The container 1 enables a flow of a treatment liquid into and out of the container 1, and a plurality of transport carriers 12 holding the containers 1 during conveyance through liquid baths 13, 14 (indicated by respective arrows) and during transfer from one liquid bath 13 (the preceding liquid bath) to another liquid bath 14 (the subsequent liquid bath), with the direction of transport generally being from left to right in the embodiment shown in FIG. 1. The contact lenses (not shown) are individually accommodated in the tube-like containers 1 which are held side-by-side in the respective transport carriers 12 (see also FIG. 2). The transport carriers 12 are conveyed along a travel path through the liquid baths 13, 14 by a conveyor 3 including a conveyor chain. For transferring the transport carriers 12 from the preceding liquid bath 13 to the subsequent liquid bath 14, the transport carriers 12 are lifted out of liquid bath 13 by conveyor 3 as shown in FIG. 1, are transported horizontally, and are then lowered again so that the containers 1 carried by the respective carrier 12 are immersed in the liquid of liquid bath 14 through which the carriers 12 are then transported. That portion of the respective container 1 (including at least a bottom 11 of the container 1) in which the contact lens is accommodated is completely immersed in the treatment liquid so that the contact lenses are exposed to the treatment liquid during the travel of the containers 1 through the respective liquid bath. Of course, instead of transporting the containers 1 from the preceding liquid bath 13 to the subsequent liquid bath 14, the containers could also be transported to a subsequent processing station other than a liquid bath. Thus, it is evident that the subsequent liquid bath 14 is one embodiment of a subsequent processing station.

The embodiment of the system shown in FIG. 1 further comprises a plurality of aspirators 2 (one for each individual container 1) having a suction cup 21 connected to a vacuum supply line 23 for applying suction 20 (see FIG. 6) to the bottom 11 of the container 1. Suction cup 21 may be formed by a solid, noncorrosive material like stainless steel or an adequate synthetic material. Also, the system comprises a positioner 4 (see again FIG. 1) for moving the respective suction cup 21 towards the bottom 11 of the respective container 1 such that the bottom 11 of the container 1 can be exposed to the suction 20 applied through the suction cup 21 during operation (see FIG. 4), however, the respective suction cup 21 is moved towards the respective container 1 only to an extent such that the suction cup 21 does not come into mechanical contact with the bottom 11 of the container 1.

As discussed already further above, during transfer from the preceding liquid bath 13 to the subsequent liquid bath 14, a carry-over of liquid from the preceding liquid bath 13 to the subsequent liquid bath 14 may result either in a change in concentration of the liquid of the subsequent liquid bath 14 (in case the subsequent liquid bath 14 is of the same kind), or may result in contamination of the liquid of the subsequent liquid bath 14 (in case the subsequent bath is of a different kind). In case of transportation of the containers 1 to a processing station other than a subsequent liquid bath 14, the liquid carried over from the liquid bath 13 may get spilled in the manufacturing line which is also unwanted.

Figure 2:
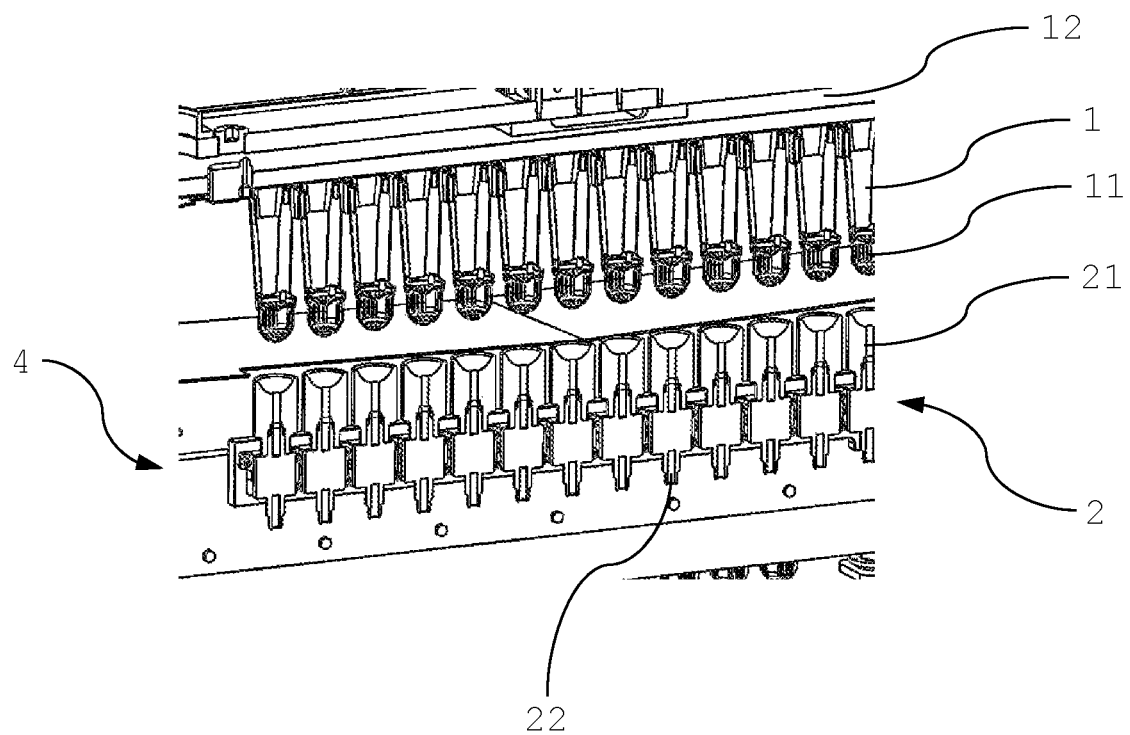
FIG. 2 is a cross-sectional view of some details of the system of FIG. 1.
Figure 3:
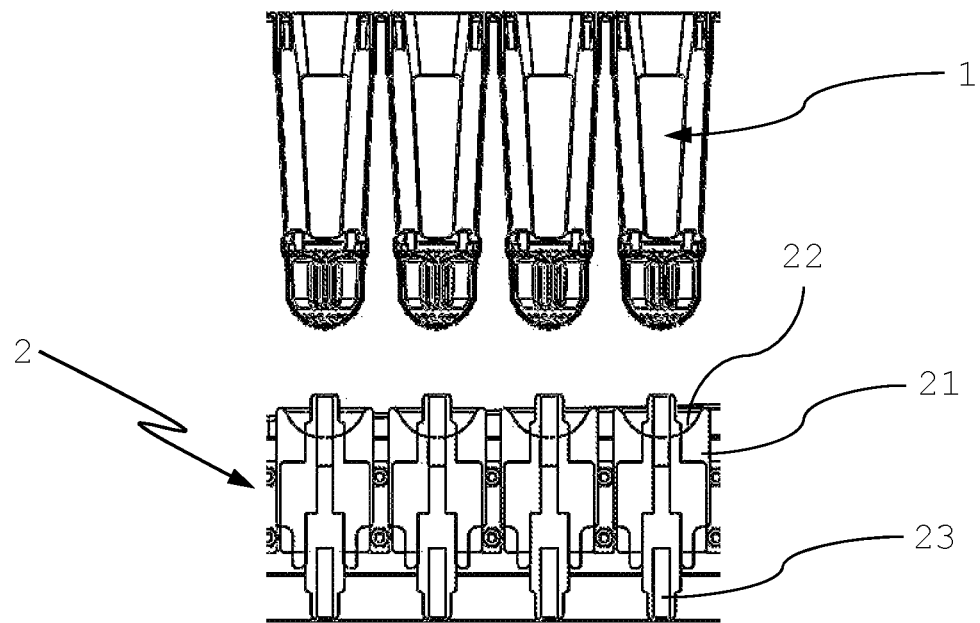
FIG. 3 is a detailed view of an arrangement of aspirators and suction cups in a position spaced apart from one another (before or after liquid removal)
Figure 4:
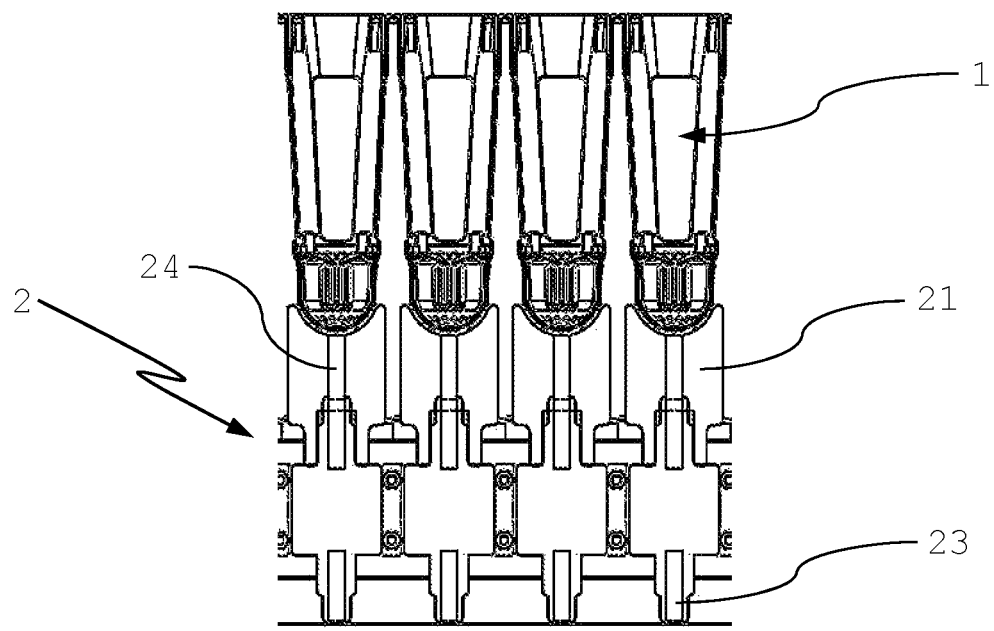
FIG. 4 is a detailed view of the arrangement of aspirators and suction cups of FIG. 3 in the operating position (during liquid removal)

To avoid such carry-over or spillage of liquid during the transport of the transport carrier 12 and the respective containers 1 from the preceding liquid bath 13 to the subsequent liquid bath 14 (or other processing station), the transport carrier 12 with the containers 1 is first arranged in a position relative to the aspirator 2 as is shown in FIG. 2 and FIG. 3, so that the bottom 11 of each individual container 1 is arranged above a corresponding suction cup 21 of the respective aspirator 2. The suction cup 21 of the respective aspirator 2 is then lifted towards the bottom 11 of the respective container 1 into a position which is shown in FIG. 4, As can be seen in FIG. 3 and FIG. 4, the aspirator 2 comprises a suction cup 21 having a central suction orifice 24 in the center of a concave wall 22 of the suction cup 21 allowing to apply suction to the convex bottom 11 of the container 1. The concave wall 22 of the suction cup 21 has a shape which corresponds to the convex shape of the bottom 11 of the container 1, so that the convexly shaped bottom 11 of the container 1 is accommodated in a cavity bounded by the concave wall 22 of the suction cup 21.

Figure 5:
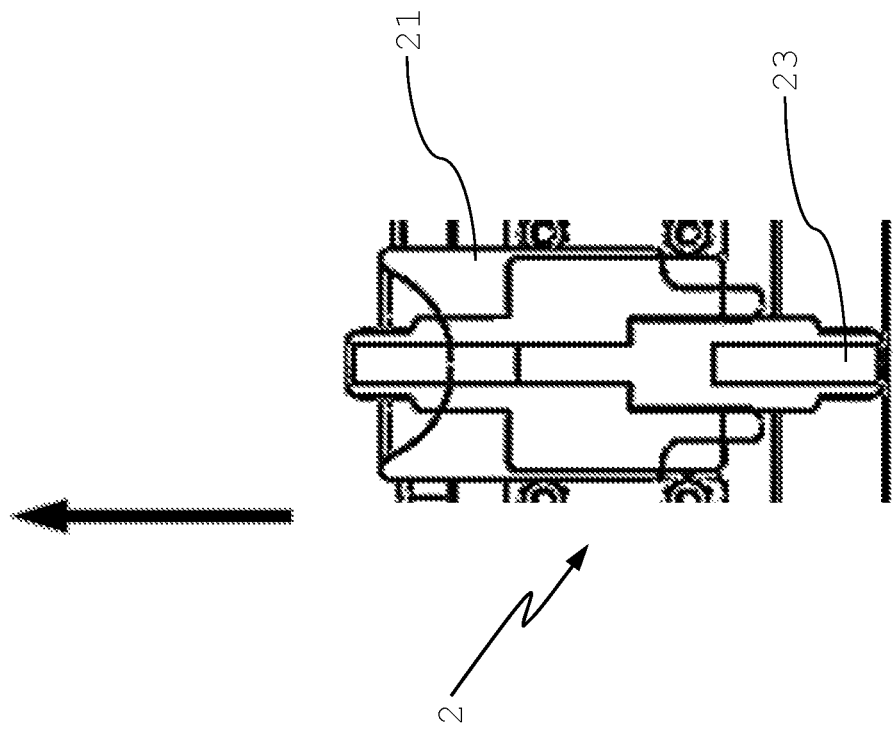
FIG. 5 is an enlarged cross-sectional side view of the aspirator with the suction cup in the spaced-apart position.

The positioner 4 comprises an actuator for linearly moving the suction cup 21 from a retracted position (FIG. 3) towards the bottom 11 of the container 1 until reaching a suction position (FIG. 4). This movement may be performed with the aid of a pneumatic linear drive, which is comprised by the positioner 4 shown in FIG. 1. This upward movement of the suction cup 21 is also indicated by the arrow shown in FIG. 5.

Once the suction cup 21 has been moved into the suction position, the concave wall 22 of the suction cup 21 is arranged in the closed vicinity of the convex bottom 11 of the container 1 but does not contact the bottom 11 of the container 1. Rather, there is a small gap between the concave wall 22 of the suction cup 21 and the convexly shaped bottom 11 of the container 1 in order to allow for air to flow through that small gap formed between the concave wall 22 of the suction cup 21 and the convexly shaped bottom 11 of the container 1.

The small gap allows for a leakage stream of air to enter between the concave wall 22 of the suction cup 21 and the convex bottom 11 of the container 1. This leakage stream flows towards the central suction orifice 24 in the concave wall 22 of the suction cup 21 and helps to transport liquid remaining on the surface of the bottom 11 of the container 1 and on the contact lens away through the vacuum supply line 23 through which the suction 20 is applied. However, the leakage stream and the suction applied are such that the remaining liquid is efficiently removed without affecting the contact lens accommodated in the container 1.

Figure 6:
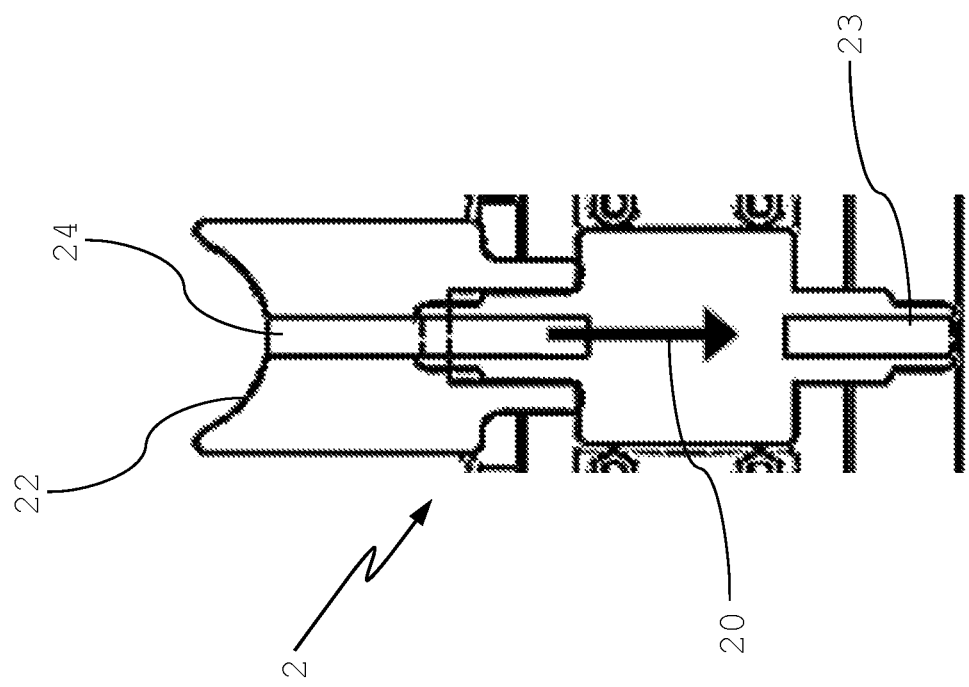
FIG. 6 is an enlarged cross-sectional side view of the aspirator of FIG. 5 with the suction cup in the operating position.

In operation, the conveyor 3 conveys the transport carrier 12 from the preceding liquid bath 13 to the subsequent liquid bath 14 (see FIG. 1). For that purpose, the transport carrier 12 with the containers 1 is lifted out of the first liquid bath 13 and is conveyed to position above the aspirators 2. Once the transport carrier 12 has reached the position above the aspirators 2 (see FIG. 2 and FIG. 3), the transport of the carrier 12 is intermitted (stopped), and the suction cups 21 are moved vertically towards the bottom 11 of the container 1 (see FIG. 5) into the suction position, however, without contacting the bottom 11 of the container 1 (see FIG. 4). Suction 20 is applied with the aid of a vacuum supply line 23 through the suction orifice 24 arranged in the concave wall 22 of the suction cup 21, as this is shown in FIG. 6. Through the application of suction 20, an air stream air is drawn through the small gap formed between the concave wall 22 of the suction cup 21 and the convexly shaped bottom 11 of the container 1 into the suction orifice 24.

By way of example only, the suction 20 may be applied to the bottom 11 of the container 1 through the suction orifice 24 in the concave wall 22 of the suction cup 21 during a time period in the range of 0.5 seconds to 2 seconds, at an air flow in the range of 2 $m^3$ to 8 $m^3$, and at a suction (underpressure) in the range of up to 900 hPa (corresponding to 900 millibars), in particular in the range of 350 hPa to 750 hPa (corresponding to 350 millibars to 750 millibars).

Once removal of the liquid has been completed, the suction cups 21 are lowered again, and movement of the transport carrier 12 with the containers 1 accommodating the contact lenses towards and into the subsequent liquid bath 14 is resumed. Through the afore-described removal of the liquid, any liquid adhering to the bottom 11 of the container or to the contact lenses is reliably drawn in through the suction orifice 24 together with the air stream, so that there is no liquid anymore that can be carried-over to the subsequent bath 14 or that can be spilled.

It has already been mentioned above, that in the treatment process for contact lenses a major contamination may arise during the conveyance of the container accommodating the contact lens between two liquid baths of different kinds. Therefore, it is advantageous to provide for a liquid removal in accordance with the invention between a water bath and a liquid bath containing an extraction liquid, or between a liquid bath containing a coating liquid and the subsequent rinsing bath, or even at the end of the liquid treatment of the contact lenses before the contact lenses are transported to the next processing station, for example to an inspection station.

The invention has been described with a reference to the particular embodiments shown in FIG. 1 to FIG. 6. However, for the skilled person it is evident that many changes and modifications can be made without departing from the general concept underlying the invention. Therefore, the scope of protection is not intended to be limited to the embodiments described but rather is defined by the appended claims.

The invention claimed is:

1. A system for removing a liquid from a container (1) for accommodating an ophthalmic lens, the system comprising:
    a transport carrier (12) comprising a container (1) having a bottom (11), the bottom having a convex shape,
    a conveyor (3) for transporting the transport carrier (12) from a liquid bath (13) to a subsequent processing station (14),
    an aspirator (2) comprising a suction cup (21) connected to a vacuum supply line (23), for applying suction (20) to the bottom (11) of the container (1),
    a positioner (4) for arranging the container (1) relative to the suction cup (21) such that the bottom (11) of the container (1) is exposed to the suction (20) applied by the suction cup (21) during operation, in order to remove the liquid from the container (1); and
    wherein the suction cup (21) of the aspirator (2) has a concave wall (22) with at least one suction orifice (24) arranged in the concave wall (22), and wherein the convex shape of the bottom (11) of the container (1) and the shape of the concave wall (22) of the suction cup correspond to allow for accommodating the convexly shaped bottom (11) of the container (1) in a cavity bounded by the concave wall (22) of the suction cup (21); and
    wherein the positioner (4) comprises an actuator for linearly moving the suction cup (21) of the aspirator (2) towards and away from the bottom (11) of the container (1).

2. The system according to claim 1, wherein the positioner (4) comprises an actuator for linearly moving the suction cup (21) of the aspirator (2) towards and away from the bottom (11) of the container (1).

3. The system according to claim 1, wherein the actuator is a pneumatic linear drive.

* * * * *